United States Patent [19]

Barratt

[11] 4,167,230
[45] Sep. 11, 1979

[54] DISPOSABLE RECEIVER

[76] Inventor: Don C. Barratt, 1255-3B Weathervane La., Akron, Ohio 44313

[21] Appl. No.: 928,251

[22] Filed: Jul. 26, 1978

[51] Int. Cl.$^2$ .................................................. A61L 17/02
[52] U.S. Cl. .................................. 206/380; 206/63.3; 206/382; 206/460; 206/818; 206/359
[58] Field of Search ............... 206/380, 382, 350, 363, 206/223, 366, 370, 460, 818, 438, 63.3, 359

[56] References Cited

U.S. PATENT DOCUMENTS

| | | | |
|---|---|---|---|
| 3,107,204 | 10/1963 | Brown et al. | 206/223 |
| 4,008,802 | 2/1977 | Freitag | 206/460 |
| 4,013,109 | 3/1977 | Sandel | 206/350 |
| 4,076,882 | 2/1978 | Fenster et al. | 206/438 |

FOREIGN PATENT DOCUMENTS 1355439  6/1974  United Kingdom ..................... 206/370

*Primary Examiner*—William T. Dixson, Jr.
*Attorney, Agent, or Firm*—James F. Cottone

[57] ABSTRACT

A receiver for securely encasing pointed disposable surgical implements comprises a tray having a bottom wall, side walls extending upwardly from the bottom wall and a flange extending outwardly around the upper periphery of the side walls. A device for receiving surgical implements is positioned on the bottom wall of the tray, and a cover having a configuration similar to the tray is hingedly connected to the tray and adapted to be folded to a closed, nested position relative to the tray with the bottom wall of the cover in close proximity to the bottom wall of the tray to securely encase surgical implements therebetween. The side walls of the cover are preferably shorter than the side walls of the tray to provide a space between the respective bottom walls to accommodate the receiving device and surgical implements.

10 Claims, 8 Drawing Figures

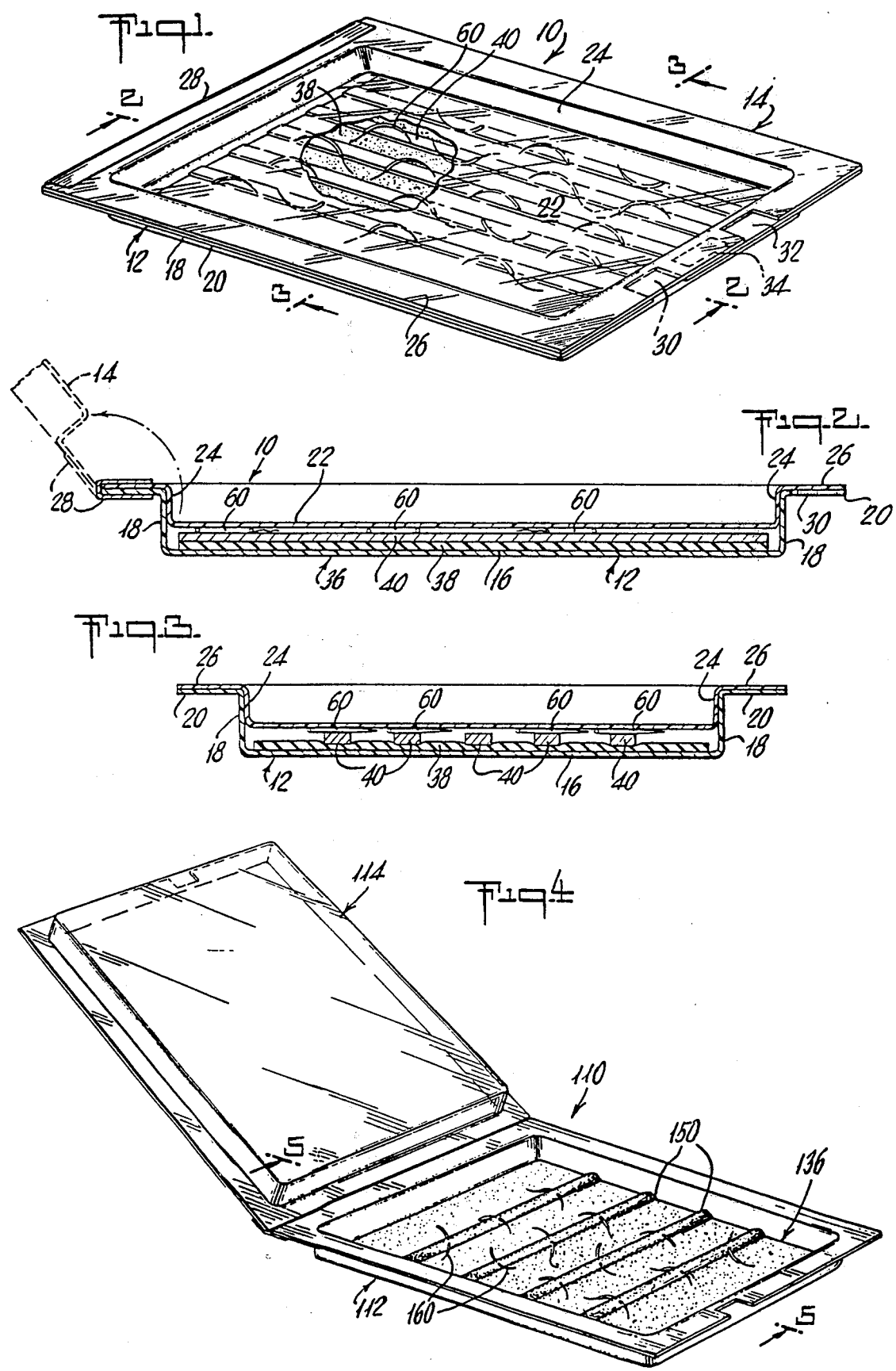

DISPOSABLE RECEIVER

BACKGROUND OF THE INVENTION

1. Field of the Invention

This invention relates to a disposable receiver for surgical implements and, more particularly, it relates to a receiver for securely encasing pointed disposable surgical implements prior to the disposal thereof.

2. Description of the Prior Art

During virtually every surgical procedure, sharp implements, such as suture needles, scalpel blades and hypodermic needles, are utilized and, following the surgical procedure, must be discarded in a safe manner. If the safety aspect of the discarding of such implements is disregarded, injury and infection of the operating room personnel may result. In order to combat this problem, many products have recently been introduced to the marketplace and many other products have been proposed in various patents.

Another serious problem attendant to the use of such sharp implements during surgery is the necessity of providing an accurate system for determining how many such implements were used and to also insure that all such implements have been accounted for following the surgical procedure. Various sharp implement count systems and devices also have been proposed to alleviate this problem.

A receiver for surgical implements utilizing a plurality of magnets which are secured to the surface of a foldable foamed elastomeric backing sheet is proposed in U.S. Pat. No. 3,727,658 to Eldridge, Jr. A similar system employing an adhesive coating on a foldable pad is described and illustrated in U.S. Pat. No. 3,944,069, also to Eldridge, Jr. Another system similar to the systems described in the two previously cited Eldridge, Jr. patents, but also providing for a method for maintaining an accurate count of the number of sharp implements utilized during the surgical procedure, is illustrated and described in U.S. Pat. No. 4,008,802 to Freitag.

In U.S. Pat. No., 4,013,109 to Sandel, a disposable container for surgical instruments is described which embodies a non-deformable casing which has magnetic sheets covering the entire surfaces of both the lower and upper portions of the case.

All of the devices described in the above-cited patents suffer from a number of disadvantages and notably among the disadvantages is the inability of the operating room personnel to make a visual inspection of the receiver or container after it has been readied for disposal. For example, although U.S. Pat. No., 4,008,802 discloses a system for maintaining a count of the used sharp implements, this count cannot be verified after the pad has been folded upon itself and adhesively secured together without again opening the pad by overcoming the force of the adhesive attachment.

Furthermore, the disposable receivers described and illustrated in the first three patents cited above are constructed so that the sharp implements are exposed at the lateral edges of the devices when they are in a folded, disposable condition. This is undesirable in that it is possible that the implements can be loosened from their attachment to the devices and either be totally dislodged from the devices or placed in an unsafe position. This condition is sought to be eliminated by the relatively rigid structure proposed in U.S. Pat. No. 4,013,109. However, this container does not provide a count system for the sharp implements nor does it supply a means for visual inspection of the implements after the container has been closed and readied for disposal.

A need exists for a system for the safe disposal of sharp surgical implements which eliminates the various disadvantages which have been experienced with previously proposed devices.

SUMMARY OF THE INVENTION

The present invention provides a receiver for securely encasing pointed disposable surgical implements which enables the operating room personnel to safely and efficiently dispose of all sharp implements utilized during a surgical procedure.

These goals are accomplished by providing a receiver in the form of a tray having a bottom wall, side walls extending upwardly from the bottom wall and a flange extending outwardly around the upper periphery of the side walls. A receiving device is positioned on the bottom wall and may take the form of a compressible foamed plastic sheet, a plurality of strip magnets or other suitable means designed to support and retain the implements within the receiver. A cover having a configuration similar to that of the tray is hingedly connected to the tray in a manner that permits the cover to be folded over and nested in the tray with the bottom wall of the cover in close proximity to the bottom wall of the tray to securely encase implements therebetween.

In the preferred embodiment of the invention, the cover is made from a transparent material to enable the operating room personnel to make a visual inspection of the sharp implements contained within the receiver after it has been closed and readied for disposal.

Also, because of the tight fit between the tray and cover, it has been found to be desirable to provide the receiver with a means for opening the cover prior to use. This may be in the form of offset notches formed at adjacent locations in the outwardly extending tray and cover flanges. In addition, these flanges may have adhesive, or other closure means, thereon to assist in the final securement of the cover to the tray prior to disposal.

BRIEF DESCRIPTION OF THE DRAWINGS

FIG. 1 is a perspective view showing one embodiment of the unique receiver of the present invention;

FIG. 2 is a cross sectional view taken along line 2—2 in FIG. 1;

FIG. 3 is a cross sectional view taken along line 3—3 in FIG. 1;

FIG. 4 is a perspective view of another embodiment of the invention illustrating the cover in an open position;

DETAILED DESCRIPTION OF THE PREFERRED EMBODIMENTS

Figure 5:
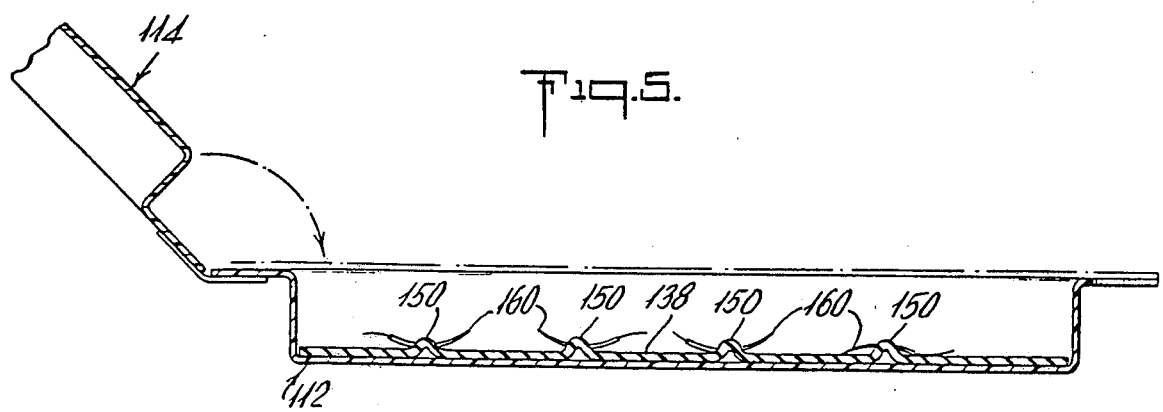
FIG. 5 is a cross sectional view taken along line 5—5 in FIG. 4.

Referring initially to FIS. 1—3, a preferred embodiment of the receiver of the present invention is illustrated generally at 10. As illustrated, receiver 10 has a generally rectangular configuration and has, as its major components, a tray 12 and a cover 14.

Tray 12 is constructed with a bottom wall 16, side walls 18 which extend upwardly from the bottom wall 16 and a flange 20 which extends outwardly around the upper periphery of side walls 18. Cover 14 has a configuration very similar to that of tray 16 and is provided with a bottom wall 22, side walls 24 and a flange 26 which extends outwardly around the upper periphery of the side walls. Although it is stated that cover 14 has a configuration virtually identical to that of tray 12, it will be appreciated that the cover, in order to be nested within tray 12 as illustrated in FIGS. 1—3, must be properly dimensioned. In addition, it will be noted that side walls 24 are shorter than side walls 18 so that, in the closed, nested position of the cover relative to the tray, bottom wall 22 will be in close proximity to bottom wall 16 to securely encase surgical implements therebetween but a space will be provided to accommodate the implements and an implement receiving means as hereinafter described. In the embodiment illustrated in FIGS. 1-3, tray 12 and cover 14 are hingedly connected together along one portion of flanges 20 and 26, respectively, by a strip of suitable tape 28 which extends over the top of flange 26 and around the edge of the flanges to the bottom of flange 20. When receiver 10 is being prepared for use, cover 14 may be opened and removed from within tray 12 by merely pivoting or folding the cover about the hinge formed by tape 28. This is illustrated in phantom in FIG. 2. In order to facilitate the opening of cover 14, adjacent notches 30 and 32 are formed in flanges 20 and 26, respectively, and serve as access and leverage points to permit an operating room attendant to pry the flanges apart and to thereby open cover 14.

A strip of pressure-sensitive adhesive 34 having an appropriate release paper placed thereover is provided on the surface of one of flanges 20 or 26 and aids in the positive securement of the flanges together after receiver 10 has been used and is being readied for disposal. It is merely necessary to remove the release paper from the adhesive in a well known manner prior to folding cover 14 into contact with tray 12.

Although tray 12 and cover 14 may be appropriately dimensioned to receive and encase surgical implements directly on bottom wall 16, it has been found to be desirable to provide a receiving means on the bottom wall to support and retain the surgical implements. In the embodiment illustrated in FIGS. 1-3, the implement receiving device is illustrated generally at 36. Device 36 may comprise a sheet 38 of foamed plastic material with a plurality of strip magnets 40 adhered to the upper surface of the sheet. Structures of this general type have been found to be particularly suitable for the retention of surgical implements of the type contemplated by this invention.

Although the specific materials used in the construction of receiver 10 are not critical, because it is intended that the receiver be a disposable item, it is desirable to construct the receiver of relatively inexpensive materials such as plastic and the like. Furthermore, the materials of construction should be relatively durable and resistant to puncture by the sharp surgical implements which may come into contact with the materials during use. Also, receiver 10 is intended for use in the sterile field during a surgical procedure and must, therefore, be sterilizable.

As previously stated, it is very desirable to provide a system for accurately determining the number of sharp surgical implements used and ultimately discarded during a surgical procedure. Therefore, it is preferred that the cover be made from a transparent material, and preferably a transparent plastic. This construction will enable the operating room personnel to make a visual inspection of the contents of receiver 10 prior to disposal of the receiver. It is contemplated that the receiver would be supplied to a hospital or other institution for use by its operating room personnel in a sterile, packaged condition. After removal from the package, the receiver may be opened by utilizing the access areas formed by notches 30 and 32, and cover 14 may then be folded or pivoted to an open position as illustrated in phantom in FIG. 2. If desired, an adhesive or other suitable securement means may be provided on the bottom of the tray to appropriately secure it to any operating room surface.

During a surgical procedure, sharp disposable surgical implements, such as needles 60 may be placed directly on magnets 40 and held firmly in place. If desired, the needles, or other sharp implements, may be removed from the magnetic surfaces for reuse and then replaced thereon for ultimate disposal. Following the completion of a surgical procedure, cover 14 can then be replaced over and nested in tray 12 with the bottom wall 22 of cover 14 in close proximity to bottom wall 16 in tray 12. Because of the dimensioning of the tray and cover, bottom wall 22 will normally contact the needles 60 and other sharp implements and hold them firmly in place against the magnets and thereby prevent shifting and dislocation of the implements. Because the implements are prevented from moving, the operating room personnel may make a visual inspection of the implements and accurately determine the number of implements contained in the receiver prior to its disposal. It should be noted that this visual inspection can be made subsequent to the final closure of the receiver. Also, it should be noted that the close fit of the side walls of the tray and cover provide an exceptionally secure container for the sharp implements and eliminates the possibility of any of the implements being dislodged from the receiver.

Figure 6:
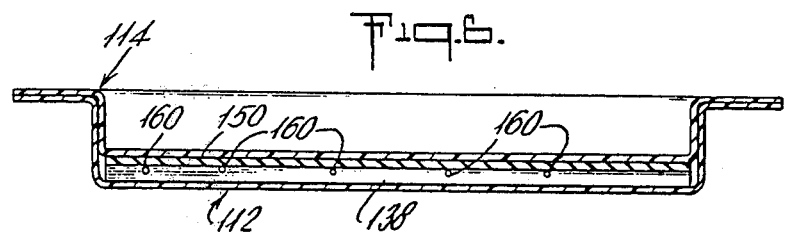
FIG. 6 is a cross sectional view taken along line 6—6 in FIG. 4.

Referring to FIGS. 4–6, another embodiment of the unique receiver of the subject invention is illustrated generally at 110. Tray 112 and cover 114 are essentailly identical to the tray and cover illustrated and described in conjunction with FIGS 1—3. However, the implement-receiving device has been modified as shown generally at 136. Referring to FIG. 5, device 136 comprises a generally flat sheet 138 of foamed plastic material into which ribs 150 have been formed. Ribs 150 may serve to securely hold needles 160 which are caused to penetrate the foam and to thereby become embedded therein. This structure provides additional security against the movement of the needles and other sharp implements within the receiver and thereby eliminates the possibility of obtaining a miscount of the implements prior to disposal.

Figure 7:
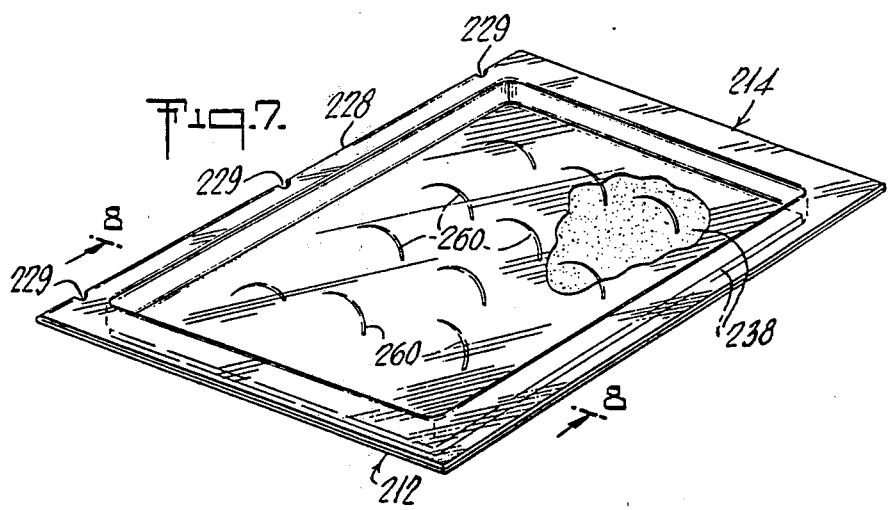
FIG. 7 is a perspective view of still another embodiment of the present invention.
Figure 8:
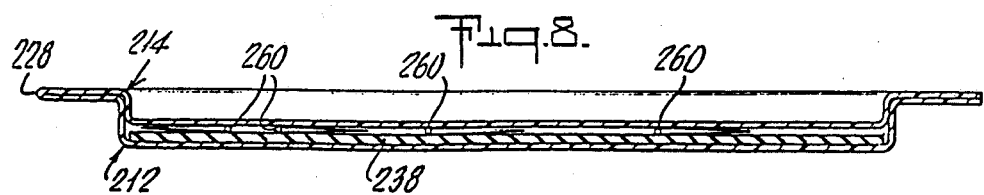
FIG. 8 is a cross sectional view taken along line 8—8 in FIG. 7.

A further embodiment of the invention is illustrated in FIGS. 7 and 8 wherein a receiver is shown having a tray 212 and a cover 214. A planar sheet 238 of yieldable foam plastic material is secured to the bottom wall of tray 212 and the upper surface of sheet 238 may be coated with a suitable pressure-sensitive adhesive onto which needles 260 and other sharp implements may be placed. The implements will be held firmly in place by the adhesive and will thereby provide an accurate count system when utilized in combination with the transparent material of which cover 214 is preferably constructed.

An additional feature illustrated in FIGS. 7 and 8 is that tray 212 and cover 214 may be formed from a single sheet of material. Hinge 228 is thereby formed by a portion of the material which is weakened by forming notches 229 along a folded edge thereof.

Although this invention has been described in detail with particular reference to certain exemplary embodiments, it is to be understood that various modifications thereof can be made by one skilled in the art and still come within the scope and spirit of the present invention which is only limited as defined in the appended claims.

What is claimed is:

1. A receiver for securely encasing pointed disposable surgical implements for disposal, comprising:
    (a) a tray having a bottom wall, side walls extending upwardly from said bottom wall and a flange extending outwardly around the upper periphery of said side walls;
    (b) a cover having a configuration similar to said tray;
    (c) a portion of the flange on said cover being hingedly connected to a portion of the flange on said tray so that said cover may be placed over and nested in said tray with the bottom wall of said cover in close proximity to the bottom wall of said tray to securely encase implements in an enclosure formed therebetween; and
    (d) means on said bottom wall for receiving said implements comprising a yieldable plastic material and occupying substantially the entire enclosure.

2. The receiver of claim 1, wherein at least said cover is transparent to permit visual inspection of said receiving means and implements encased therein.

3. A receiver for securely encasing pointed disposable surgical implements for disposal, comprising:
    (a) a generally rectangular tray having a bottom wall, four side walls extending upwardly from said bottom wall and a flange extending outwardly from the upper periphery of said side walls;
    (b) a generally rectangular cover having a bottom wall, four side walls extending upwardly from said bottom wall, and a flange extending outwardly from the upper periphery of said side walls;
    (c) said tray flange along one side wall being hingedly connected to said cover flange along one side wall so that said cover and said tray may be folded from a substantially coplanar position to a closed, nested position with the bottom wall of said cover in close proximity to the bottom wall of said tray to securely encase implements in an enclosure formed therebetween; and
    (d) means on said bottom wall for receiving said implements comprising a yieldable plastic material and occupying substantially the entire formed enclosure.

4. The receiver of claim 3, further comprising means on said tray and cover flanges for securing said tray and cover together when placed in the closed, nested position.

5. The receiver of claim 4, wherein said securing means is a pressure sensitive adhesive on one flange which adheres to the other flange when said tray and cover are placed in the closed, nested position.

6. The receiver of claim 3, wherein said cover is transparent to permit visual inspection of said receiving means and implements encased therein.

7. The receiver of claim 3, wherein the side walls of said cover are shorter than the side walls of said tray to provide a space between the respective bottom walls to accomodate said receiving means and implements.

8. The receiver of claim 7, wherein said receiving means further comprises a plurality of thin strip magnets attached to said plastic material for assisting in the retention of said implements.

9. The receiver of claim 3, wherein the tray flange and cover flange have adjacent notches formed therein which are nonaligned to facilitate the opening of said cover relative to said tray.

10. The receiver of claim 2 or claim 6, wherein said receiving means further comprises a thin layer of adhesive attached to said plastic material for assisting in the retention of said implements.

* * * * *